US008575404B2

(12) United States Patent
Jevtic et al.

(10) Patent No.: US 8,575,404 B2
(45) Date of Patent: Nov. 5, 2013

(54) PROCESS FOR RECYCLING GAS FROM ACETIC ACID HYDROGENATION

(75) Inventors: Radmila Jevtic, Pasadena, TX (US); Victor J. Johnston, Houston, TX (US); R. Jay Warner, Houston, TX (US); John Potts, Angleton, TX (US); Stephen Kerlegon, League City, TX (US)

(73) Assignee: Celanese International Corporation, Dallas, TX (US)

( * ) Notice: Subject to any disclaimer, the term of this patent is extended or adjusted under 35 U.S.C. 154(b) by 287 days.

(21) Appl. No.: 13/078,727

(22) Filed: Apr. 1, 2011

(65) Prior Publication Data

US 2012/0010441 A1 Jan. 12, 2012

Related U.S. Application Data

(60) Provisional application No. 61/332,696, filed on May 7, 2010.

(51) Int. Cl.
*C07C 29/149* (2006.01)
(52) U.S. Cl.
USPC .......................................................... 568/885
(58) Field of Classification Search
USPC .......................................................... 568/885
See application file for complete search history.

(56) References Cited

U.S. PATENT DOCUMENTS

| | | | |
|---|---|---|---|
| 2,649,407 A | 8/1953 | Harrison et al. |
| 2,702,783 A | 2/1955 | Harrison et al. |
| 2,744,939 A | 5/1956 | Kennel |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,395,576 A | 7/1983 | Kwantes et al. |
| 4,398,039 A | 8/1983 | Pesa et al. |
| 4,421,939 A | 12/1983 | Kiff et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,541,897 A | 9/1985 | Sommer et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,842,693 A | 6/1989 | Wheldon |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,124,004 A | 6/1992 | Grethlein et al. |
| 5,144,068 A | 9/1992 | Smith et al. |
| 5,149,680 A | 9/1992 | Kitson et al. |
| 5,185,308 A | 2/1993 | Bartley et al. |
| 5,215,902 A | 6/1993 | Tedder |
| 5,233,099 A | 8/1993 | Tabata et al. |
| 5,237,108 A | 8/1993 | Marraccini et al. |
| 5,250,271 A | 10/1993 | Horizoe et al. |
| 5,449,440 A | 9/1995 | Rescalli et al. |
| 5,565,068 A | 10/1996 | Parker et al. |
| RE35,377 E | 11/1996 | Steinberg et al. |
| 5,599,976 A | 2/1997 | Scates et al. |
| 5,770,770 A | 6/1998 | Kim et al. |
| 5,821,111 A | 10/1998 | Grady et al. |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,375,807 B1 | 4/2002 | Nieuwoudt et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,115,772 B2 | 10/2006 | Picard et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |

(Continued)

FOREIGN PATENT DOCUMENTS

EP 2060553 A1 5/2009

(Continued)

OTHER PUBLICATIONS

English Abstract for WO 2008/135192, Nov. 13, 2008.

(Continued)

*Primary Examiner* — Sikarl Witherspoon

(57) ABSTRACT

Monitoring and recycling gases from acetic acid hydrogenation reaction to maintain a constant pressure in the hydrogenation reaction system. Purging of the vapor stream comprising hydrogen may be limited or reduced. Further purging of the by-product may be from the dissolved by-product gases.

27 Claims, 9 Drawing Sheets

(56) References Cited

U.S. PATENT DOCUMENTS

| | | |
|---|---|---|
| 7,208,624 B2 | 4/2007 | Scates et al. |
| 7,297,236 B1 | 11/2007 | Vander et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,732,173 B2 | 6/2010 | Mairal et al. |
| 7,863,489 B2 | 1/2011 | Johnston et al. |
| 8,071,389 B2 | 12/2011 | Weck et al. |
| 2006/0019360 A1 | 1/2006 | Verser et al. |
| 2007/0270511 A1 | 11/2007 | Melnichuk et al. |
| 2008/0135396 A1 | 6/2008 | Blum |
| 2009/0014313 A1 | 1/2009 | Lee et al. |

FOREIGN PATENT DOCUMENTS

| | | |
|---|---|---|
| EP | 2060555 | 5/2009 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | 2009063176 | 5/2009 |
| WO | WO 2009/105860 | 9/2009 |
| WO | WO 2010/055285 | 5/2010 |

OTHER PUBLICATIONS

International Search Report and Written Opinion for PCT/US2011/035564 mailed Jan. 25, 2012.

International Preliminary Report on Patentability mailed Aug. 7, 2012 in corresponding International Application No. PCT/US2011/035564.

PROCESS FOR RECYCLING GAS FROM ACETIC ACID HYDROGENATION

CROSS REFERENCE TO RELATED APPLICATIONS

This application claims priority to U.S. Provisional Application No. 61/332,696, filed on May 7, 2010, the entire content and disclosure of which is incorporated herein by reference.

FIELD OF THE INVENTION

The present invention relates generally to processes for producing and/or purifying ethanol and, in particular, to processes for controlling non-condensable gas from the hydrogenation of acetic acid.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as biofuels. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

Excess of hydrogen is used to increase the yield of ethanol production in converting carbonaceous feedstock into low-molecular weight alcohols. Due to the use of excess amounts of hydrogen, it is beneficial to recycle the unreacted hydrogen back to the reactor. However, additional gases are also formed during the reaction, such as methane, ethane, nitrogen, carbon monoxide, and carbon dioxide, that would build-up reactor when hydrogen is recycled. EP2060555 describes purging the gas recycle stream to control the build up of the gases in the hydrogenation reactor. Purging the gas recycle stream results in the lost of the reactants for the reaction and reduces operating efficiencies.

However, a need remains for improving the processes for controlling non-condensable gas from the hydrogenation of acetic acid to increase production of ethanol.

SUMMARY OF THE INVENTION

In a first embodiment, the present invention is directed to a process for producing ethanol, comprising hydrogenating acetic acid from an acetic acid feed stream in a reactor in the presence of a catalyst to form a crude ethanol product comprising ethanol; separating at least a portion of the crude ethanol product to yield a vapor stream and a liquid stream, wherein the vapor stream comprises unreacted hydrogen and at least one by-product gas, and wherein the liquid stream comprises ethanol; purging less than 15% of the vapor stream in a first purge stream; returning at least a portion of the vapor stream directly or indirectly to the reactor; and recovering ethanol from the liquid stream.

In a second embodiment, the present invention is directed to a process for producing ethanol comprising hydrogenating acetic acid from an acetic acid feed stream in a reactor in the presence of a catalyst to form a crude ethanol product comprising ethanol; separating at least a portion of the crude ethanol product to yield a vapor stream and a liquid stream, wherein the vapor stream comprises unreacted hydrogen and carbon monoxide in an amount less than 2 mol. %, and wherein the liquid stream comprises ethanol; returning at least a portion of the vapor stream directly or indirectly to the reactor; and recovering ethanol from the liquid stream.

In a third embodiment, the present invention is directed to a process for producing ethanol comprising hydrogenating acetic acid from an acetic acid feed stream and a hydrogen feed stream in a reactor system in the presence of a catalyst to form a crude ethanol product comprising ethanol; separating at least a portion of the crude ethanol product to yield a vapor stream and a liquid stream, wherein the vapor stream comprises unreacted hydrogen, and wherein the liquid stream comprises ethanol; returning at least a portion of the vapor stream directly or indirectly to the reactor; measuring a pressure of the vapor stream or a pressure of the at least a portion of the vapor stream; controlling pressure in the reactor system by regulating the feed of fresh hydrogen to the reactor in response to the measured pressure; and recovering ethanol from the liquid stream.

In a fourth embodiment, the present invention is directed to a process for producing ethanol comprising hydrogenating acetic acid from an acetic acid feed stream in a reactor in the presence of a catalyst to form a crude ethanol product comprising ethanol; separating the crude ethanol product to yield a vapor stream and a liquid stream, wherein the vapor stream comprises unreacted hydrogen and at least one by-product gas, and wherein the liquid stream comprises ethanol; withdrawing a slip stream from the vapor stream; purging a portion of the slip stream when the concentration of one of the at least one by-product gases is greater than 5 mol. %; and recovering ethanol from the liquid stream.

In a fifth embodiment, the present invention is directed to a process for producing ethanol comprising hydrogenating acetic acid from an acetic acid feed stream in a reactor in the presence of a catalyst to form a crude ethanol product comprising ethanol; separating at least a portion of the crude ethanol product to yield a vapor stream and a liquid stream, wherein the vapor stream comprises unreacted hydrogen and at least one by-product gas, and wherein the liquid stream comprises ethanol and at least one dissolved by-product gas; purging the at least one dissolved by-product gas from the liquid stream; and recovering ethanol from the liquid stream.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
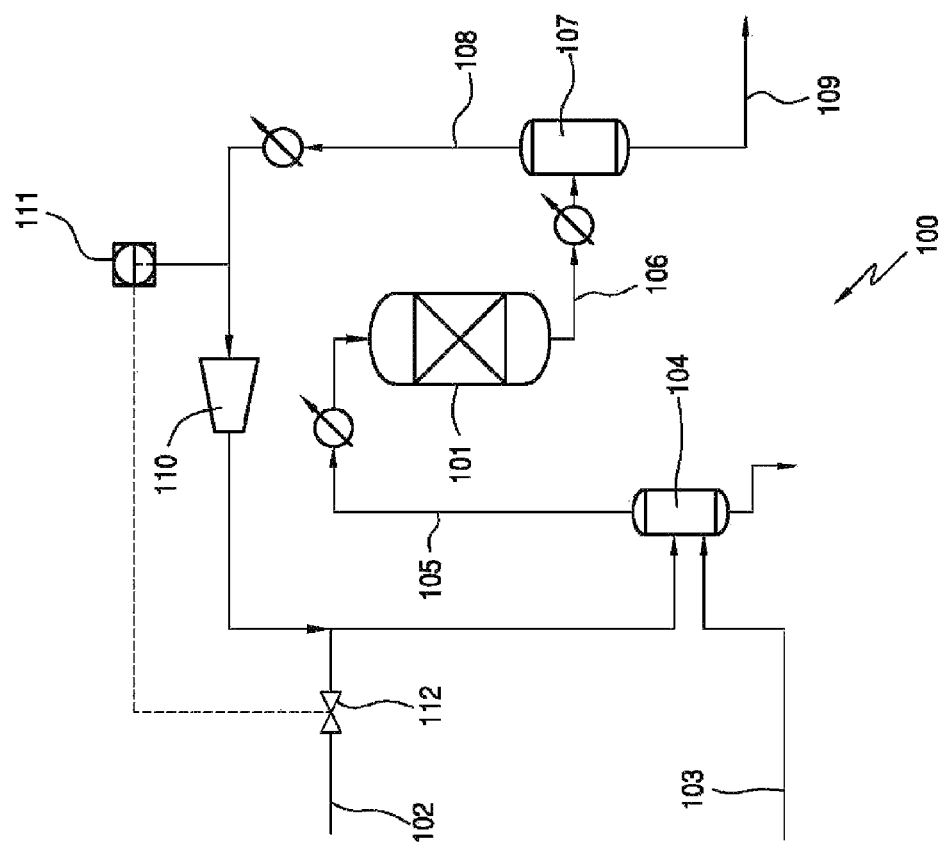
FIG. 1 is a schematic diagram of the reaction zone in accordance with one embodiment of the present invention.

The present invention relates to processes for recovering ethanol produced by a hydrogenation process comprising hydrogenating acetic acid in the presence of a catalyst. In particular, the present invention relates to recovering and/or purifying ethanol from a crude ethanol product preferably produced by the hydrogenation process. The process includes a step of recycling unreacted hydrogen gas in a recycled vapor stream from the crude reaction mixture by returning it to the reaction process, preferably to the reactor. The returned hydrogen may be reacted under hydrogenation conditions to make additional ethanol. In one embodiment, portions of the unreacted hydrogen and the non-condensable gaseous byproducts are purged from the crude ethanol product and the lost volume may be replaced by fresh hydrogen gas. This may dilute harmful gaseous by-products in the recycled vapor stream for the hydrogenation process. In another embodiment, the system pressure may be maintained at a steady level by controlling the fresh hydrogen level, such that fresh hydrogen may be added to replenish the hydrogen consumed during the hydrogenation process or to replace the volume of the purged gas. Embodiments of the present invention beneficially may be used in applications for recovering and/or purifying ethanol on an industrial scale.

The hydrogenation of acetic acid forms equal molar ratios of ethanol and water. Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

When excess of hydrogen is used, thermal decomposition of acetic acid, water-gas shift reaction and ethanol dehydration occur and form undesirable by-products, such as methane, ethane, carbon monoxide and carbon dioxide (Formulas I-IV):

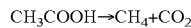
$$CH_3COOH \rightarrow CH_4 + CO_2 \quad \text{I}$$

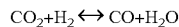
$$CO_2 + H_2 \leftrightarrow CO + H_2O \quad \text{II}$$

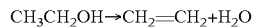
$$CH_3CH_2OH \rightarrow CH_2=CH_2 + H_2O \quad \text{III}$$

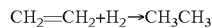
$$CH_2=CH_2 + H_2 \rightarrow CH_3CH_3 \quad \text{IV}$$

The by-product gases may be harmful to certain types of hydrogenation catalysts and may lead to the formation of further impurities in the ethanol. Conventionally, it is understood to purge the gas recycle line to remove the by-product gases. Surprisingly and unexpectedly, the inventors have found that the levels of by-product gases in the reactor reach a steady state when the gas recycle line is recycled without a purge. Without being bound by theory, the by-product gases are dissolved in the liquid phase and may be vented after separation in one or more columns. Thus, hydrogen may be effectively recycled while by-product gases may be removed from the process. In addition, a smaller purge may be used to remove by-product gases from the gas recycle line.

The process of the present invention may be used with any ethanol production, preferably with ethanol produced by acetic acid hydrogenation. The materials, catalyst, reaction conditions, and separation are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In a similar manner, hydrogen for the hydrogenation step may be supplied from syn gas.

In some embodiments, some or all of the raw materials for the above-described acetic acid hydrogenation process may be derived partially or entirely from syngas. For example, the acetic acid may be formed from methanol and carbon monoxide, both of which may be derived from syngas. For example, the methanol may be formed by steam reforming syngas, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the entire disclosures of which are incorporated herein by reference. Optionally, the production of ethanol may be integrated with such methanol carbonylation processes.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111 which discloses a process for converting waste biomass through gasification into synthesis gas, and U.S. Pat. No. 6,685,754, which discloses a method for production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol according to one embodiment of the invention may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal, or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. Nos. 7,608,744 and 7,863,489 and U.S. Pub. No. 2010/0197485, the entireties of which are incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. Most preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another, or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal is preferably from 0.05 to 4 wt. %, e.g., from 0.1 to 3 wt. %, or from 0.1 to 2 wt. %.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include siliceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 $m^2$/g; median pore diameter of about 12 nm; average pore volume of about 1.0 $cm^3$/g as measured by mercury intrusion porosimetry; and packing density of about 0.352 $g/cm^3$ (22 $lb/ft^3$).

A preferred silica/alumina support material is KA-160 silica spheres from Süd-Chemie having a nominal diameter of about 5 mm, a density of about 0.562 g/ml, an absorptivity of about 0.583 g $H_2O$/g support, a surface area of about 160 to 175 $m^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour, or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 grams of ethanol per kilogram catalyst per hour or from 600 to 2,000 grams of ethanol per kilogram catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 15 tons of ethanol per hour, preferably at least 30 tons of ethanol per hour. In terms of ranges, for large scale industrial production of ethanol, the process of the present invention may produce 15 to 160 tons of ethanol per hour, e.g., 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid optionally is present in the crude ethanol product in an amount from 0 to 90 wt. %, e.g., from 5 to 80 wt. %, from 15 to 70 wt. %, from 20 to 70 wt. % or from 25 to 65 wt. %. As water is formed in the reaction process, water will generally be present in the crude ethanol product, for example, in amounts ranging from 5 to 35 wt. %, e.g., from 10 to 30 wt. % or from 10 to 26 wt. %.

Ethyl acetate may also be produced during the hydrogenation of acetic acid, or through side reactions and may be present, for example, in amounts ranging from 0 to 20 wt. %, e.g., from 0 to 15 wt. %, from 1 to 12 wt. % or from 3 to 10 wt. %. In addition, acetaldehyde may be produced through side reactions, and may be present, for example, in amounts ranging from 0 to 10 wt. %, e.g., from 0 to 3 wt. %, from 0.1 to 3 wt. % or from 0.2 to 2 wt. %. Other components, such as, for example, alcohols, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

Figure 2:
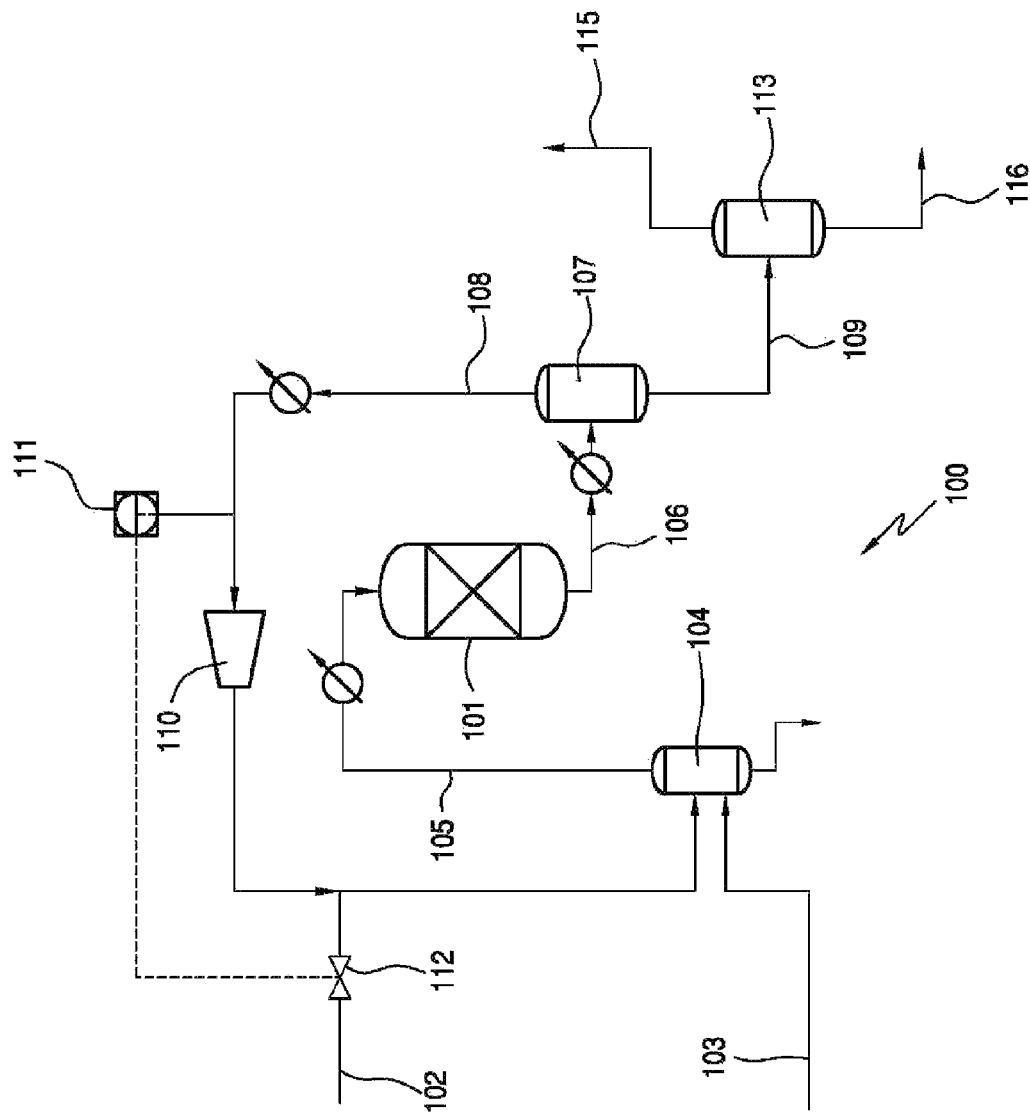
FIG. 2 is a schematic diagram of the reaction zone in accordance with one embodiment of the present invention.
Figure 3:
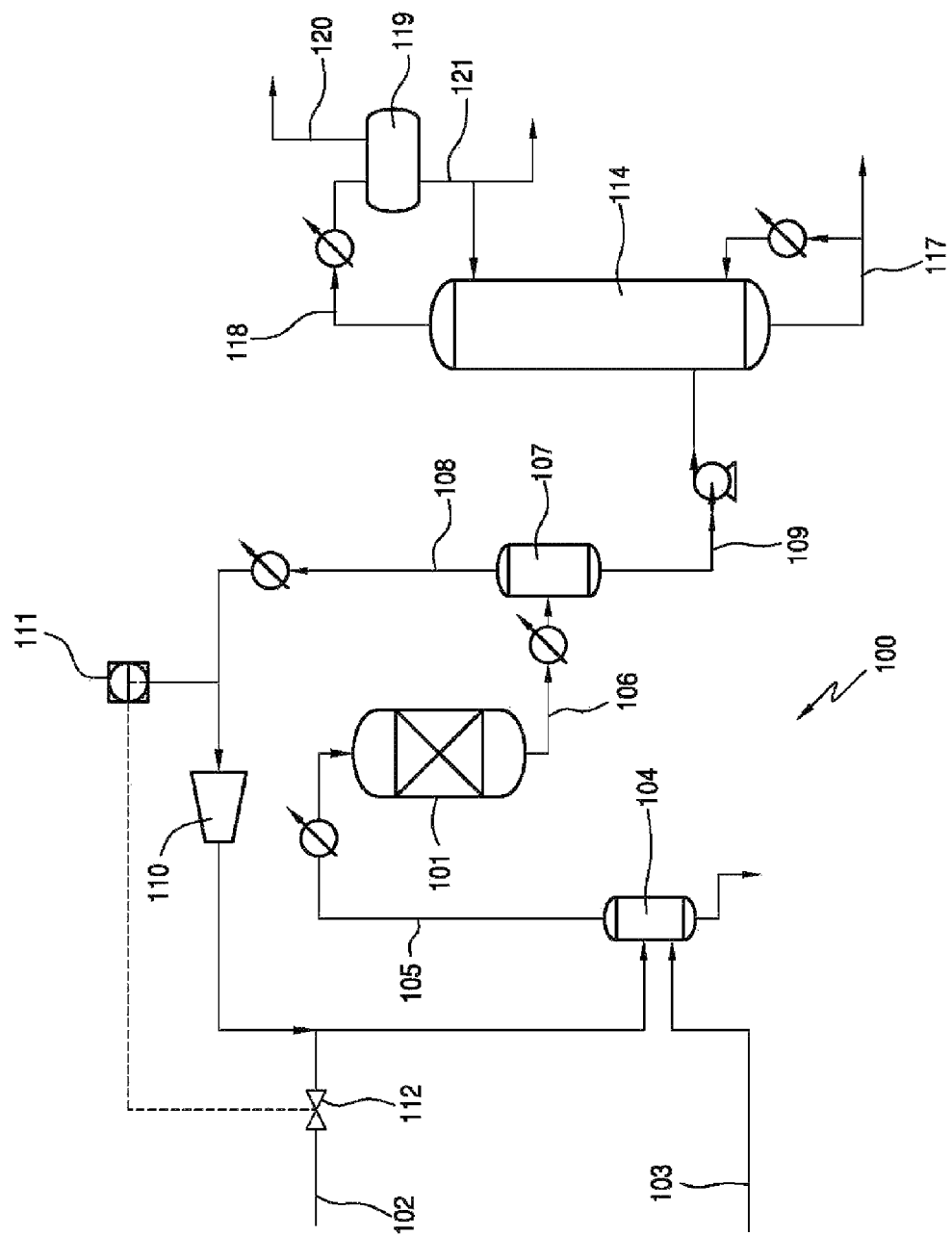
FIG. 3 is a schematic diagram of the reaction zone in accordance with one embodiment of the present invention.

FIGS. 1-3 show a reaction zone 100 of a hydrogenation system suitable for the hydrogenation of acetic acid to form ethanol according to one embodiment of the present invention. Reaction zone 100 comprises a reactor 101, hydrogen feed line 102 and acetic acid feed line 103. Hydrogen and acetic acid are fed to a vaporizer 104 via lines 102 and 103, respectively, to create a vapor feed stream in line 105 that is directed to reactor 101. Trace amount of nitrogen also may be present in one or both of the feed streams. In one embodiment, lines 102 and 103 may be combined and jointly fed to the vaporizer 104. The temperature of the vapor feed stream in line 105 is preferably from 100° C. to 350° C., e.g., from 120° C. to 310° C. or from 150° C. to 300° C. Any feed that is not vaporized is removed from vaporizer 104, as shown in FIG. 1, and may be recycled thereto. In addition, although FIG. 1 shows line 105 being directed to the top of reactor 101, line 105 may be directed to the side, upper portion, or bottom of reactor 101.

Reactor 101 contains the catalyst that is used in the hydrogenation of the carboxylic acid, preferably acetic acid. During the hydrogenation process, a crude ethanol product is withdrawn, preferably continuously, from reactor 101 via line 106. The crude ethanol product may be condensed and fed to flasher 107, which, in turn, provides a vapor stream 108 and a liquid stream 109. The flasher 107 in one embodiment preferably operates at a temperature of from 50° C. to 500° C., e.g., from 70° C. to 400° C. or from 100° C. to 350° C. In one embodiment, the pressure of flasher 107 preferably is from 50 KPa to 2000 KPa, e.g., from 75 KPa to 1500 KPa or from 100 to 1000 KPa. In one preferred embodiment the temperature and pressure of the flasher 107 is similar to the temperature and pressure of the reactor 101.

Vapor stream 108 exiting the flasher 107 may comprise hydrogen, and by-product gases, such as methane, ethane, nitrogen, carbon monoxide and carbon dioxide. The vapor stream contains unreacted hydrogen in an amount between 90 to 100 mol. %, e.g., between 92 to 98 mol. %, or between 93 to 97 mol. % and contains by-product gases in an amount less than 10 mol. %, e.g., less than 5 mol. %, less than 3 mol. %, or less than 1 mol. %. In one embodiment, the by-product gases are selected from the group consisting of methane, ethane, carbon dioxide, carbon monoxide, nitrogen, and mixtures thereof. Methane concentration may be less than 3 mol. %, e.g., less than 1.5 mol. % or less than 1.2 mol. %. Ethane concentration may be less than 3 mol. %, e.g., less than 1 mol. % or less than 0.8 mol. %. Carbon dioxide concentration may be less than 3 mol. %, e.g., less than 0.8 mol. % or less than 0.5 mol. %. Carbon monoxide concentration may be less than 2 mol. %, e.g., less than 0.3 mol. %, or less than 0.2 mol. %. Nitrogen concentration may be less than 2 mol. %, e.g., less than 0.4 mol. %, or less than 0.3 mol. %.

In an embodiment of the invention, unreacted hydrogen, along with by-product gases, is recycled and is returned to reactor 101 via recycle line 108, preferably without a purge. Furthermore, recycle line 108 may be combined with fresh hydrogen 102 before being fed to vaporizer 104. The pressure of recycle line 108 generally is lower than the reactor 101, and recycle line 108 is passed through a compressor 110. To maintain constant pressure in reactor 103, a pressure analyzer 111 may measure the pressure of recycle line 108 and control the amount of fresh hydrogen 102 via valve 112. Pressure analyzer 111 may operate continuously. Generally, the pipeline pressure of fresh hydrogen 102 may be sufficient to supply the pressure for the reactor 101. As indicated above, the pressure of the reactor 101 may be from 10 KPa to 3000 KPa, and constant pressure refers to maintaining a pressure that varies by less than 5%, e.g., less than 3% or less than 1%. For example, if the reactor pressure is 100 KPa, the constant pressure is within 95 to 105 KPa. Although pressure analyzer 111 is shown before compressor 110 in FIG. 1, in some embodiments, pressure analyzer may be after compressor 110.

As stated above, by-product gases, such as methane, ethane, carbon monoxide, carbon dioxide, and/or nitrogen, may be dissolved in the liquid stream 109 exiting flasher 107. Depending on the solubility limit of the by-product gas or mixtures of gases, the concentration of the dissolved by-product gases may vary. The solubility of a gas in a liquid depends on temperature, the partial pressure of the gas over the liquid, the nature of the liquid and the nature of the gas. As used herein, the term "dissolved by-product gas" or "dissolved by-product gases" refers to a dissolved material that is a gas at 1 atmospheric pressure and room temperature.

In one embodiment, the dissolved by-product gases, such as methane, ethane, carbon monoxide, carbon dioxide and/or nitrogen, in a concentration from 0.00001 to 0.1 wt. %, e.g., 0.0001 to 0.01 wt. % or 0.001 to 0.005 wt. %. Liquid stream 109 may be further separated to recover ethanol. The dissolved by-product gases may be vented from liquid stream 109. In FIG. 2, the dissolved by-product gases are vented in a second flasher 113. In FIG. 3, the dissolved by-product gases are vented from the overhead of a distillation column 114. In some embodiments, there may be purge of by-product gases in both a second flasher 113 as shown in FIG. 2 and from the overhead of distillation column 114. As used herein, the term "purge" may mean purging of a substance in either a liquid or a vapor form.

In an embodiment of the invention shown in FIG. 2, liquid stream 109 is fed to a second flasher 113, which, in turn, provides a second vapor stream 115 and a second liquid stream 116. As a result, light-weight, by-product gases, i.e., methane, carbon monoxide and carbon dioxide, may be purged from the system. Second flasher 113 may operate at a lower temperature and/or pressure than flasher 107. In one embodiment, the temperature of second flasher 113 preferably is from 20° C. to 100° C., e.g., from 30° C. to 85° C. or from 40° C. to 70° C. In one embodiment, the temperature of second flasher 113 preferably is at least 50° C. lower than first flasher 107, e.g., at least 75° C. lower or at least 100° C. lower. The pressure of second flasher 107 preferably is from 0.1 KPa to 1000 KPa, e.g., from 0.1 KPa to 500 KPa or from 0.1 KPa to 100 KPa. In one embodiment, the pressure of second flasher 107 preferably is at least 50 KPa lower than first flasher 107, e.g., at least 100 KPa lower or at least 200 KPa lower.

Second vapor stream 115 may comprise at least 1 mol. % by-product gases, e.g., at least 5 mol. % or at least 10 mol. %. Preferably these by-product gases are vented from the system. Second liquid stream 116 may be further separated to recover ethanol. Preferably, second liquid stream 116 contains less dissolved by-product gases than liquid stream 109.

In another embodiment of the invention shown in FIG. 3, liquid stream 109 is fed to a distillation column 114. In distillation column 114, liquid stream is separated to recover ethanol. Depending on the acetic acid conversion and operation of column 114, unreacted acetic acid, water, and other heavy components, if present, are removed from the composition in line 117 and are withdrawn, preferably continuously, as residue. In some embodiments, especially with higher conversions of acetic acid of at least 80%, or at least 90%, it may be beneficially to remove a majority of water in line 117 along with substantially all the acetic acid in residue stream 117. Residue stream 117 may be recycled to reaction zone 100. In addition, a portion of the water in residue stream 117 may be separated and purged with the acid rich portion being returned to reaction zone 100. In other embodiments, the residue stream 117 may be a dilute acid stream that may be treated in a weak acid recovery system or sent to a reactive distillation column to convert the acid to esters.

Column 114 also forms an overhead distillate, which is withdrawn in line 118, and which may be condensed and collected in an overhead receiver 119. A vent stream 120 may be withdrawn from receiver 119 to remove by-product gases, such as methane, ethane, carbon monoxide, carbon dioxide, nitrogen and mixtures thereof. Vent stream 120 may comprise at least 1 mol. % by-product gases, e.g., at least 5 mol. % or at least 10 mol. %. The liquid stream 121 from receiver 119 may be refluxed, for example, at a ratio of from 10:1 to 1:10, e.g., from 3:1 to 1:3 or from 1:2 to 2:1. Preferably, ethanol may be recovered from the liquid stream 121.

In FIGS. 1-3, vapor stream 108 is recycled to reactor 101 preferably without a purge. Preferably, by-product gases are purged from the dissolved gases in the liquid stream 109. In some embodiments, there may be a smaller purge from vapor stream 108, e.g., less than 5% of vapor stream 108 is purged, e.g., less than 1% or less than 0.5%. Generally, when smaller purges are taken it is still preferable to purge a majority of the by-products through the second flasher in FIG. 2 or from the overhead in FIG. 3. However, in some embodiments a larger purge of less than 15% of vapor stream, e.g. less than 10% or less than 8%, may be taken. Thus, at least 85% of the gases separated from the crude ethanol product are returned to the reactor via vapor stream 108 and more preferably at least 90%, e.g., at least 92% or at least 99%.

Figure 4:
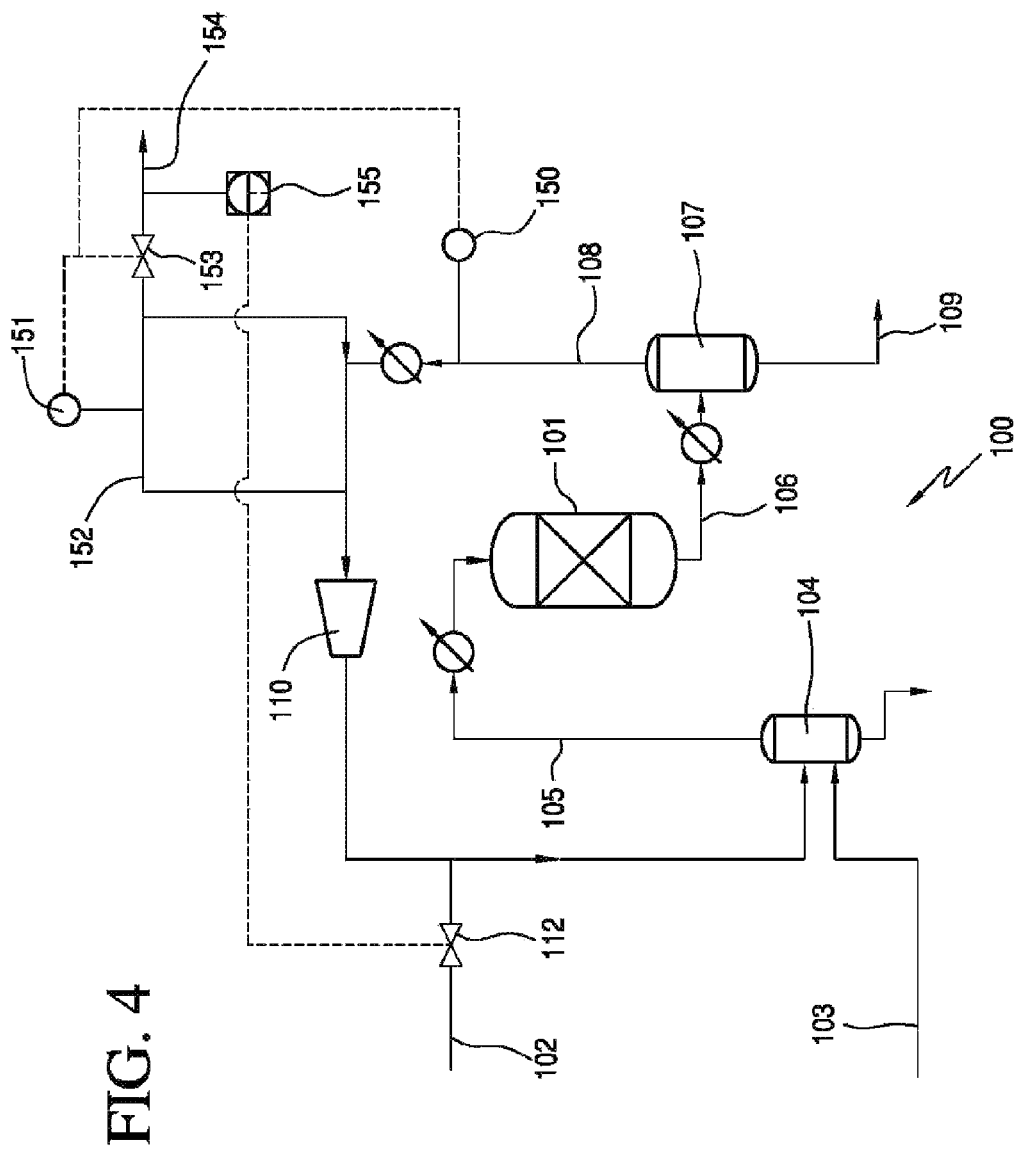
FIG. 4 is a schematic diagram of the reaction zone and recycling of gas in accordance with one embodiment of the present invention.

In FIG. 4, there is provided a reaction zone 100 having analyzers 150 and/or 151 for measuring the composition of vapor stream 108 that exits flasher 109. Analyzers 150 measures the composition of vapor stream 108 directly. Analyzers 151 measure the content of a slipstream 152 of vapor stream 108. In some embodiments, a reaction zone may comprise either analyzer 150 or analyzer 151. When any of the by-product gases exceeds a threshold value, analyzers 150 or 151 communicate with a control system to operate valve 153 to release a purge stream 154. A pressure analyzer 155 may monitor the purge stream 154 to control the amount of fresh hydrogen 102 via valve 112, and thus maintain a constant pressure reaction zone 100.

Analyzers are widely used to monitor vapor streams by on-line gas chromatography, GC/MS, on-line infrared spectroscopy, NIR, FTNIR, UV, Visible light, LED, laser or mass spectrometry. An on-line gas chromatography or infrared spectroscopy may be used to analyze the vapor stream 108 for one of the by-product gases, e.g., methane, ethane, carbon monoxide, or carbon dioxide. The on-line techniques may be backed up by daily samples to cross check on-line analysis. A mass spectrometric analyzer may required a sample from vapor stream 108 and may be used with slipstream 152 to detect the concentration of the by-product gases. In one embodiment, analyzer 150 may be an on-line analyzer and analyzer 151 may be an on-line analyzer or a mass spectrometric analyzer. In a preferred embodiment, on-line techniques are used to monitor the concentration of the by-product gases.

Once the concentration of one or more of the by-product gases exceeds a threshold value, the analyzer communicates with the controller to release a purge stream 154 by opening valve 153. As shown in FIG. 4, purge stream 154 is taken from slipstream 151. In other embodiments, purge stream may be taken directly from vapor stream 108. The threshold value is a preset or controllable value that may be monitored to release by-products from vapor stream 108. The threshold value may be different for each by-product gas. In addition, there may a total threshold value for all the by-product gases. For example, the threshold value for all the by-product gases may be at least 5 mol. %, e.g., at least 8 mol. %, or at least 10 mol. %. Also, the threshold value for any of the by-product gases may at least 5 mol. %, e.g., at least 8 mol. %, or at least 10 mol. %. In some embodiments, the amount for individual gases may be lower When the analyzers 150 or 151 detect a concentration of by-product gases that exceeds at least 1 mol. %, the valve is opened to release a purge stream 154. The amount of vapor stream 108 that is purged may depend on the concentration of the by-product gases in vapor stream. Thus, in some embodiments, more than 1% of the vapor stream is purged, e.g., more than 3% or more than 5%. Preferably, less than 15% of vapor stream is purged when a by-product gas exceeds a threshold value, e.g. less than 10% or less than 8%.

Suitable threshold values for each of the by-product gases are as follows. It is understood, that depending on the operation of the reaction system 100, other threshold values may be selected. For methane, suitable threshold values include greater than 1.2 mol. %, e.g., greater than 1.5 mol. % or greater than 3 mol. %. For ethane, suitable threshold values include greater than 0.8 mol. %, e.g., greater than 1 mol. % or greater than 3 mol. %. For carbon monoxide, suitable threshold values include greater than 0.5 mol. %, e.g., greater than 0.8 mol. % or greater than 3 mol. %. For carbon dioxide, suitable threshold values include greater than 0.2 mol. %, e.g., greater than 0.3 mol. % or greater than 2 mol. %. Carbon monoxide is a known catalyst poison and monitoring carbon monoxide concentrations may be advantageous to prevent recycling large amounts of carbon monoxide that may cause reactor inefficiencies.

An advantage to using analyzers 150 or 151 is that vapor stream 108 is purged when by-product gases are present in larger concentrations. This allows a majority of the hydrogen to be recycled without a substantially lose of reactants. In an embodiment of the present invention, preferably, less than 15 mol. % of the by-product gases is purged from the system. More preferably, there is substantially no purge in the system.

Figure 5:
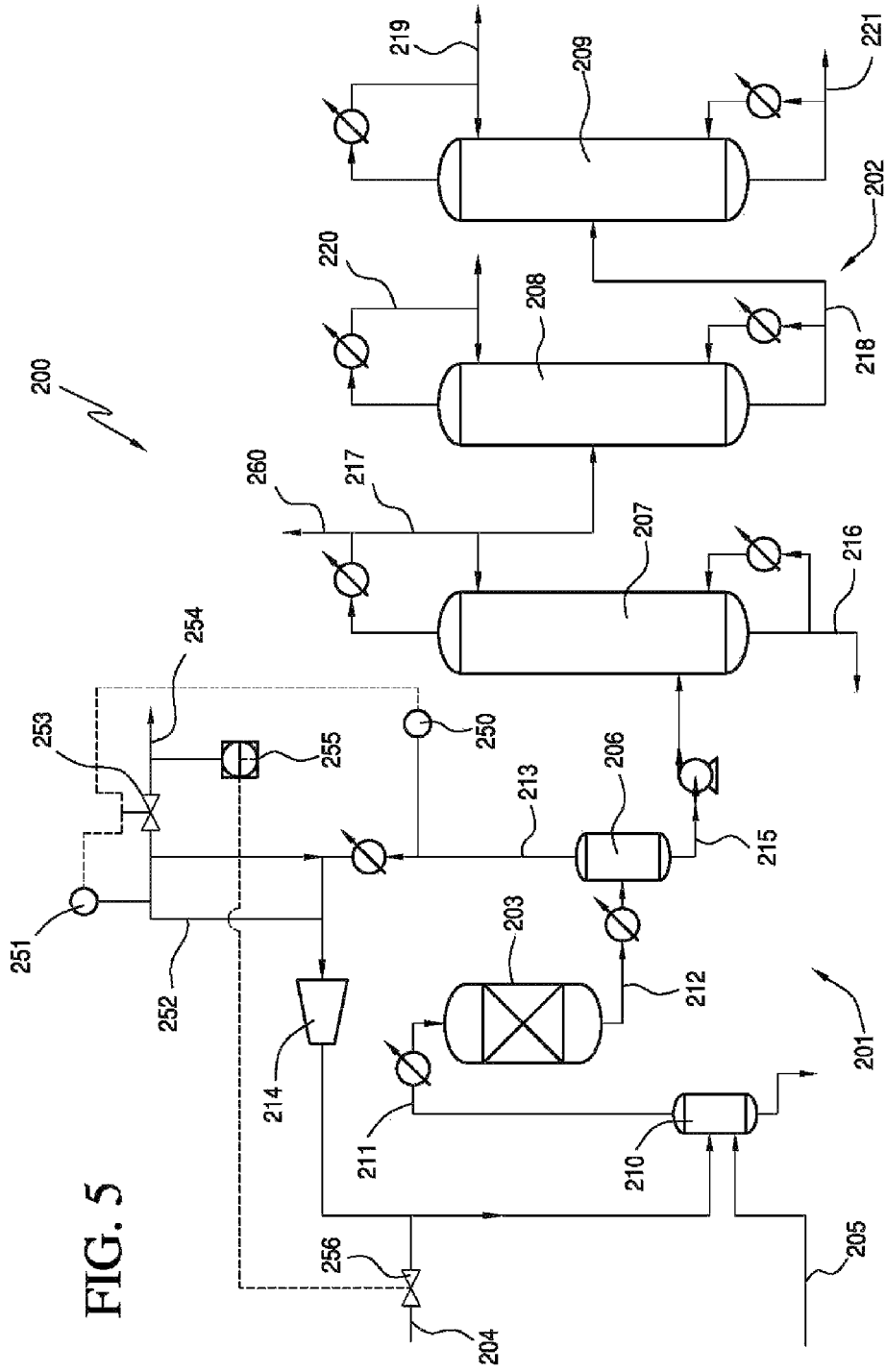
FIG. 5 is a schematic diagram of a hydrogenation system in accordance with one embodiment of the present invention.

A hydrogenation system 200 suitable for the hydrogenation of acetic acid and separating ethanol from the crude reaction mixture according to one embodiment of the present invention is shown in FIG. 5. The system 200 comprises reaction zone 201 and distillation zone 202. The exemplary system in FIG. 5 is shown with the reaction zone from FIG. 4, but it should be appreciated that any of the reactor zones from FIGS. 1-3 may be used in the hydrogenation system.

Hydrogen and acetic acid are fed to a vaporizer 210 via lines 204 and 205, respectively, to create a vapor feed stream in line 211 that is directed to reactor 203. In one embodiment, lines 204 and 205 may be combined and jointly fed to the vaporizer 210, e.g., in one stream containing both hydrogen and acetic acid. The temperature of the vapor feed stream in line 211 is preferably from 100° C. to 350° C., e.g., from 120° C. to 310° C. or from 150° C. to 300° C. Any feed that is not vaporized is removed from vaporizer 210, as shown in FIG. 2, and may be recycled thereto. In addition, although FIG. 2 shows line 211 being directed to the top of reactor 203, line 211 may be directed to the side, upper portion, or bottom of reactor 203. Further modifications and additional components to reaction zone 201 are described below.

Reactor 203 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In certain embodiments of the invention, the guard bed media is functionalized to trap particular species such as sulfur or halogens. During the hydrogenation process, a crude ethanol product is withdrawn, preferably continuously, from reactor 203 via line 212.

The crude ethanol product may be condensed and fed to flasher 206, which, in turn, provides a vapor stream and a liquid stream. The flasher 206 may operate at a temperature of from 30° C. to 500° C., e.g., from 70° C. to 400° C. or from 100° C. to 350° C. The pressure of flasher 206 may be from 50 KPa to 2000 KPa, e.g., from 75 KPa to 1500 KPa or from 100 to 1000 KPa. In another embodiment, the temperature and pressure of the flasher is similar to the temperature and pressure of the reactor 203.

The vapor stream 213 exiting the flasher 206 may comprise hydrogen and by-product gases. A reaction zone 200 having analyzers 250 and/or 251 for measuring the composition of vapor stream 213 that exits flasher 206. Analyzers 250 measures the composition of vapor stream 213 directly. Analyzers 251 measure the content of a slipstream 252 of vapor stream 209. In some embodiments, a reaction zone may comprise either analyzer 250 or analyzer 251. When any of the by-product gases exceeds a threshold value, analyzers 250 or 251 communicate with a control system to operate valve 253 to release a purge stream 254. A pressure analyzer 255 may monitor the purge stream 254 to control the amount of fresh hydrogen 204 via valve 256, and thus maintain a constant pressure reaction zone 200. In one embodiment, vapor stream 213 preferably comprises by-products having a concentration below the threshold value and no purge is necessary from vapor stream 213. The remaining vapor stream 213 that is not purged passes through compressor 214 and is returned to reactor 203.

The liquid from flasher 206 is withdrawn and pumped as a feed composition via line 215 to the side of first column 207, also referred to as the acid separation column. In one embodiment, liquid stream 215 may contain dissolved by-product gases and hydrogen. In one embodiment, the dissolved by-product gases, such as methane, ethane, carbon monoxide, carbon dioxide and/or nitrogen, in a concentration amount from 0.00001 to 0.1 wt. %, e.g., 0.0001 to 0.01 wt. % or 0.001 to 0.005 wt. %. The contents of line 215 typically will be substantially similar to the product obtained directly from the reactor, and may, in fact, also be characterized as a crude ethanol product. Generally a large amount of hydrogen may be removed by flasher 206. Exemplary components of liquid in line 215 are provided in Table 2. It should be understood that liquid line 215 may contain other components, not listed, such as components in the feed.

TABLE 2

FEED COMPOSITION

|  | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 3 may include, but are not limited to, ethyl propionate, methyl acetate, isopropyl acetate, n-propyl acetate, n-butyl acetate or mixtures thereof. The "other ethers" in Table 3 may include, but are not limited to, diethyl ether, methyl ethyl ether, isobutyl ethyl ether or mixtures thereof. The "other alcohols" in Table 3 may include, but are not limited to, methanol, isopropanol, n-propanol, n-butanol or mixtures thereof. In one embodiment, the feed composition, e.g., line 215, may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, the crude ethanol product may be fed directly to the acid separation column as a vapor feed and the by-product gases may be purged from a vent from the overhead of the column 207.

When the content of acetic acid in line 215 is less than 5 wt. %, the acid separation column 207 may be skipped and line 215 may be introduced directly to second column 208, also referred to herein as a "light ends column".

In the embodiment shown in FIG. 2, line 215 is introduced in the lower part of first column 207, e.g., lower half or lower third. Depending on the acetic acid conversion and operation of column 207, unreacted acetic acid, water, and other heavy components, if present, are removed from the composition in line 215 and are withdrawn, preferably continuously, as residue. In some embodiments, especially with higher conversions of acetic acid of at least 80%, or at least 90%, it may be beneficially to remove a majority of water in line 215 along with substantially all the acetic acid in residue stream 216. Residue stream 216 may be recycled to reaction zone 201. In addition, a portion of the water in residue stream 216 may be separated and purged with the acid rich portion being returned to reaction zone 201. In other embodiments, the residue stream 216 may be a dilute acid stream that may be treated in a weak acid recovery system or sent to a reactive distillation column to convert the acid to esters.

First column 207 also forms an overhead distillate, which is withdrawn in line 217, and which may be condensed and collected in an overhead receiver (not shown). A vent stream 260 may be withdrawn from receiver to remove by-product gases, such as methane, ethane, carbon monoxide, carbon dioxide, nitrogen and mixtures thereof. Vent stream 120 may comprise at least 1 mol. % by-product gases, e.g., at least 5 mol. % or at least 10 mol. %. Preferably it is desirable to remove the by-product gases dissolved in liquid stream 215 after the first column 207. A liquid stream from received may be refluxed, for example, at a ratio of from 10:1 to 1:10, e.g., from 3:1 to 1:3 or from 1:2 to 2:1.

The columns shown in FIGS. 1-5, may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIG. 5. As shown in FIG. 5, heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in FIG. 5, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 KPa to 3000 KPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

When column 207 is operated under standard atmospheric pressure, the temperature of the residue exiting in line 216 from column 207 preferably is from 95° C. to 120° C., e.g., from 105° C. to 117° C. or from 110° C. to 115° C. The temperature of the distillate exiting in line 217 from column 207 preferably is from 70° C. to 110° C., e.g., from 75° C. to 95° C. or from 80° C. to 90° C. In other embodiments, the pressure of first column 207 may range from 0.1 KPa to 510 KPa, e.g., from 1 KPa to 475 KPa or from 1 KPa to 375 KPa. In one exemplary embodiment a distillate and residue compositions for first column 207 are provided in Table 3 below, excluding by-product gases. Note that these compositions may change depending on acetic acid conversion, the operation of the column and whether a majority of the water is removed in the residue. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

|  | Conc. (wt. %) | Conc. (wt. %) | Conc. (wt. %) |
|---|---|---|---|
| Distillate |  |  |  |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue |  |  |  |
| Acetic Acid | 60 to 100 | 70 to 95 | 85 to 92 |
| Water | <30 | 1 to 20 | 1 to 15 |
| Ethanol | <1 | <0.9 | <0.07 |

Some species, such as acetals, may decompose in column 207 to low or even no detectable amounts. In addition, there may be a non-catalyzed equilibrium reaction after the crude ethanol product 212 exits the reactor 203 in liquid feed 215. Depending on the concentration of acetic acid, the equilibrium may be driven towards formation of ethyl acetate. The equilibrium may be regulated using the residence time and/or temperature of liquid feed 215.

The first distillate in line 217 preferably comprises ethanol, ethyl acetate, and water, along with other impurities, which may be difficult to separate due to the formation of binary and tertiary azeotropes. The first distillate in line 217 is introduced to the second column 208, also referred to as the "light ends column," preferably in the middle part of column 208, e.g., middle half or middle third. Second column 208 may be a tray column or packed column. In one embodiment, second column 208 is a tray column having from 5 to 70 trays, e.g., from 15 to 50 trays or from 20 to 45 trays. As one example, when a 25 tray column is utilized in a column without water extraction, line 217 is introduced at tray 17. In one embodiment, the second column 208 may be an extractive distillation column. In such embodiments, an extraction agent, such as water, may be added to second column 208. If the extraction agent comprises water, it may be obtained from an external source or from an internal return/recycle line from one or more of the other columns.

In some embodiments, a portion of the water in first distillate 217 may be removed prior to second column 208, using one or more membranes, and/or adsorptions units.

Although the temperature and pressure of second column 208 may vary, when at atmospheric pressure the temperature of the second residue exiting in line 218 from second column 208 preferably is from 60° C. to 90° C., e.g., from 70° C. to 90° C. or from 80° C. to 90° C. The temperature of the second distillate exiting in line 220 from second column 208 preferably is from 50° C. to 90° C., e.g., from 60° C. to 80° C. or from 60° C. to 70° C. Column 208 may operate at atmospheric pressure. In other embodiments, the pressure of second column 208 may range from 0.1 KPa to 510 KPa, e.g., from 1 KPa to 475 KPa or from 1 KPa to 375 KPa. Exemplary components for the distillate and residue compositions for second column 208 are provided in Table 4 below. It should be understood that the distillate and residue may also contain other components, not listed, such as components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 5 to 70 | 30 to 60 | 30 to 50 |
| Ethanol | 20 to 95 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 208, the weight ratio of ethyl acetate in the second residue to ethyl acetate in the second distillate approaches zero.

Returning to the second distillate 220, which comprises ethyl acetate and/or acetaldehyde, preferably is refluxed as shown in FIG. 2, for example, at a reflux ratio of from 1:10 to 10:1, e.g., from 1:5 to 5:1 or from 1:3 to 3:1. The second distillate 220 or portion thereof may be returned reactor 203. In some embodiments, it may be advantageous to return a portion of second distillate 220 to reactor 203 when no acetic acid is returned via first residue 216 to reactor 203. In one embodiment, second distillate may be fed via line 220 to acetaldehyde removal column (not shown) to recover aldehyde that may be recycled to the reactor 203. Second distillate 220 may also be hydrolyzed or fed to an hydrogenolysis reactor to produce ethanol from ethyl acetate. Additionally, second distillate 220 may be purged from system.

As shown, the second residue from the bottom of second column 208, which comprises ethanol and water, is fed via line 218 to third column 209, also referred to as the "product column" More preferably, the second residue in line 218 is introduced in the lower part of third column 209, e.g., lower half or lower third. Third column 209 recovers ethanol, which preferably is substantially pure other than the azeotropic water content, as the distillate in line 219. The distillate of third column 209 preferably is refluxed as shown in FIG. 2, for example, at a reflux ratio of from 1:10 to 10:1, e.g., from 1:3 to 3:1 or from 1:2 to 2:1. The third residue in line 221, which preferably comprises primarily water, preferably is removed from the system 200 or may be partially returned to any portion of the system 200. Third column 209 is preferably a tray column as described above and preferably operates at atmospheric pressure. The temperature of the third distillate exiting in line 219 from third column 209 preferably is from 60° C. to 110° C., e.g., from 70° C. to 100° C. or from 75° C. to 95° C. The temperature of the third residue exiting from third column 209 preferably is from 70° C. to 115° C., e.g., from 80° C. to 110° C. or from 85° C. to 105° C., when the column is operated at atmospheric pressure. Exemplary components of the distillate and residue compositions for third column 209 are provided in Table 5 below. It should be understood that the distillate and residue may also contain other components, not listed, such as components in the feed.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 207, 208 and/or 209 in the system 200. Preferably at least one side stream is used to remove impurities from the third column 209. The impurities may be purged and/or retained within the system 200.

The ethanol product is taken from the third distillate 219. Third distillate 219 may be further purified to form an anhydrous ethanol product stream, i.e., "finished anhydrous ethanol," using one or more additional separation systems, such as, for example, distillation columns (e.g., a finishing column), membranes, adsorption units, or molecular sieves. Anhydrous ethanol may be suitable for fuel applications.

The final ethanol product by the present invention may be taken from the third distillate 219. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 6.

TABLE 6

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 7, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including application as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y.

Zeolite X is described, for example, in U.S. Pat. No. 2,882, 244 and zeolite Y in U.S. Pat. No. 3,130,007, the entireties of which are hereby incorporated herein by reference.

In order that the invention disclosed herein may be more efficiently understood, an example is provided below. The following examples describe the various distillation processes of the present invention.

EXAMPLES

The system was set up to measure the accumulation rate of gaseous byproducts in the recycle gas. Pressure for the initial reactions was set at 300 psig. Temperature for the system was set at 300° C. The acetic acid flow rate was set at 3.56 ml/min acetic acid and the recycle flow rate was set at 10 L/min. Initially, the acid flow rate was set to zero and the vent line open to 100% to purge all the gases, but hydrogen, from the loop. The presence of hydrogen was monitored using an online gas chromatographer (GC). Once it was determined that only hydrogen was present in the system, the vent was closed and the acetic acid flow line was opened. The accumulation of gaseous byproducts in the recycle loop was measured for 24-hours and shown in FIG. 6.

Figure 6:
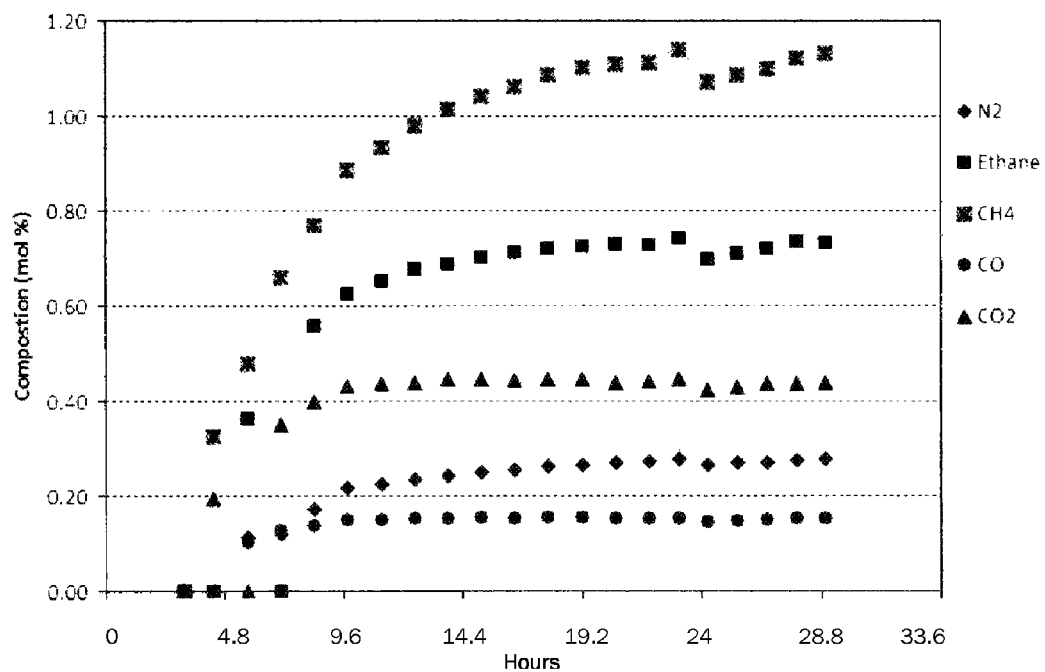
FIG. 6 is a graph showing the build up of gaseous by-products over a 24-hour period in the recycle loop of hydrogenation process.

As shown in FIG. 6, the main products in the recycle loop are methane, ethane, carbon monoxide and carbon dioxide. The by-product components build up rapidly on the closing of the valve, but then reach a steady-state composition. For example, carbon monoxide appears to have reached a steady state after about five hours and remained at a 0.20 mol. % concentration during the next 19 hours of the experiment. Similarly, nitrogen, carbon dioxide, ethane and methane all reached a plateau after about 5-11 hours.

Figure 7:
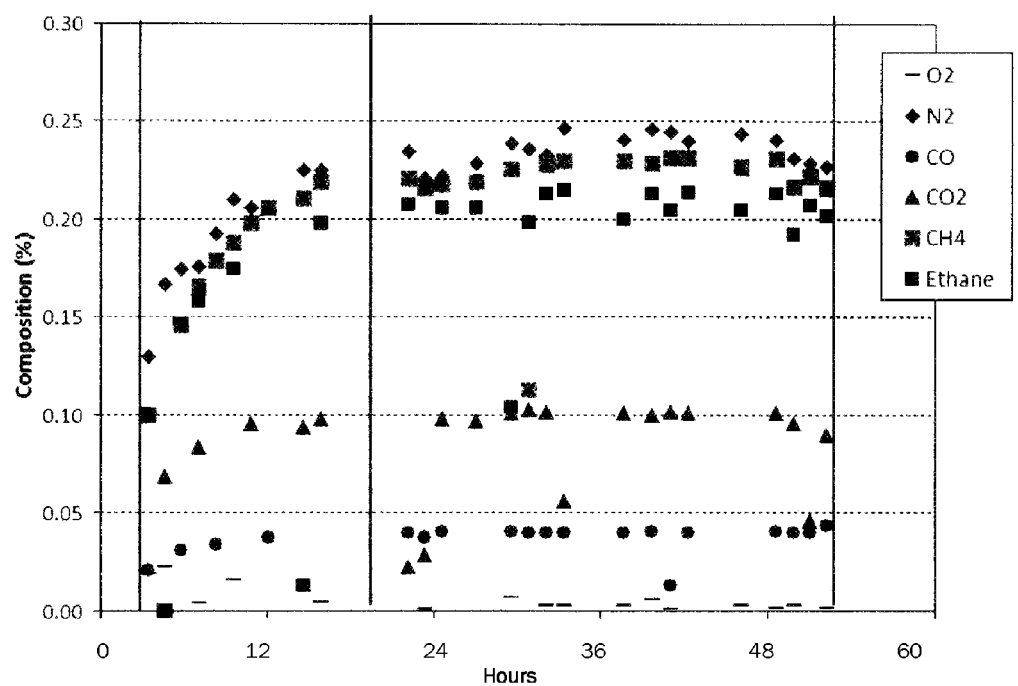
FIG. 7 is a graph showing the build up of gaseous by-products over a 3-day period at 300° C. in the recycle loop of hydrogenation process.

The experiment above was repeated and the reactions were monitored over the course of 3-days, as shown in FIG. 7. The accumulation of gaseous byproducts in the recycle loop was measured at three different intervals (as indicated by the vertical line) to determine the effect of the gaseous byproducts in the recycle loop over time. The conversions and selectivities are shown in Table 7.

TABLE 7

| | Conversion | Selectivity (%) | | | |
|---|---|---|---|---|---|
| | (%) | EtOH | EtOAc | AcH | DEA |
| Sample 1 | 38.19 | 88.88 | 8.95 | 1.74 | 0.43 |
| Sample 2 | 36.60 | 88.92 | 8.88 | 1.67 | 0.52 |
| Sample 3 | 36.44 | 89.33 | 8.49 | 1.74 | 0.44 |

As shown in Table 7, the selectivities of the reactor products appeared to be unaffected by the accumulation of the gaseous byproducts. The conversion seemed to be slightly higher at the beginning of the experiment when the level of the components in the recycled gas loop was low. The temperature profile during the experiment was steady and thus temperature did not play a role in the selectivities of the reactor products.

Figure 8:
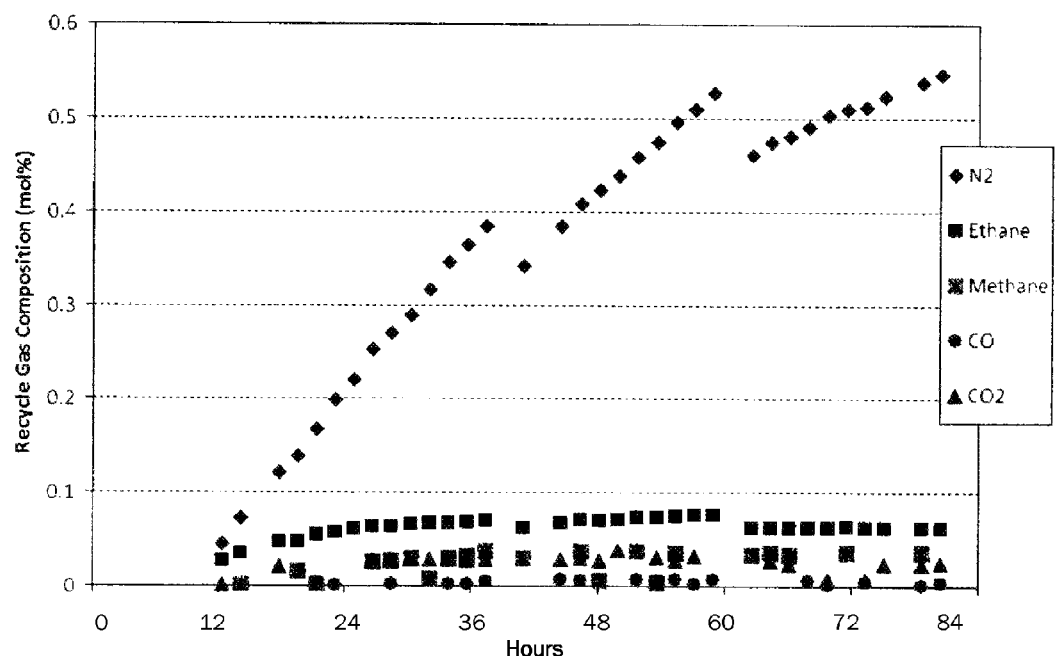
FIG. 8 is a graph showing the build up of gaseous by-products over a 3-day period at 250° C. in the recycle loop of hydrogenation process.
Figure 9:
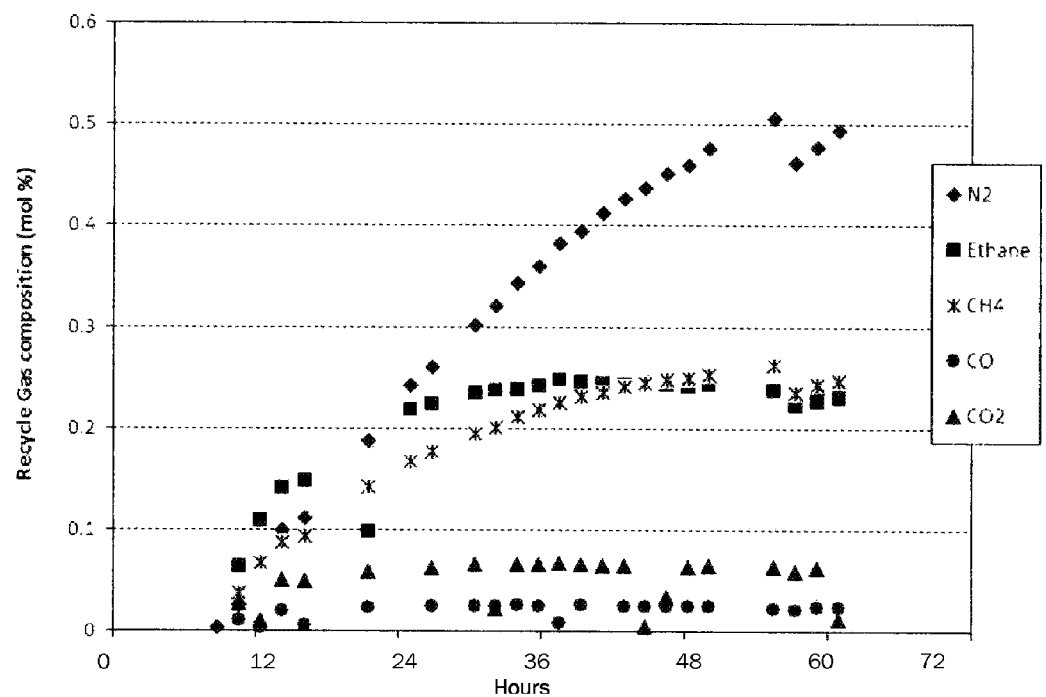
FIG. 9 is a graph showing the build up of gaseous by-products over a 3-day period at 275° C. in the recycle loop of hydrogenation process.

The experiment was repeated at 250° C. and 275° C. The results of these experiments is shown in FIG. 8 and FIG. 9, respectively. As shown in both figures, all components expect nitrogen reached steady state after roughly 12 hours. It is believed that nitrogen entered the system through the liquid feed line.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol comprising the steps of:
    hydrogenating acetic acid from an acetic acid feed stream in a reactor in the presence of a catalyst to form a crude ethanol product comprising ethanol;
    separating at least a portion of the crude ethanol product to yield a vapor stream and a liquid stream, wherein the vapor stream comprises unreacted hydrogen and at least one by-product gas, and wherein the liquid stream comprises ethanol and at least one dissolved by-product gas;
    purging less than 15% of the vapor stream in a first purge stream;
    purging at least a portion of at least one dissolved by-product gas from the liquid stream to form a second purge stream;
    returning at least a portion of the vapor stream directly or indirectly to the reactor; and
    recovering ethanol from the liquid stream.

2. The process of claim 1, further comprising purging less than 1% of the vapor stream in the first purge stream.

3. The process of claim 1, further comprising purging less than 0.01% of the vapor stream in the first purge stream.

4. The process of claim 1, wherein the at least one by-product gas is selected from a group consisting of methane, ethane, carbon monoxide, carbon dioxide, nitrogen and mixtures thereof.

5. The process of claim 1, wherein the at least one by-product gas comprises methane, and wherein the vapor comprises the methane in an amount from 0.01 to 3 mol. %.

6. The process of claim 1, wherein the at least one by-product gas comprises carbon monoxide, and wherein the vapor stream comprises the carbon monoxide in an amount from 0.01 to 2 mol. %.

7. The process of claim 1, wherein the liquid stream comprises the at least one dissolved by-product gas in an amount from 0.001 to 0.1 wt. %.

8. The process of claim 1, wherein the second purge stream comprises said at least one by-product gases in an amount greater than 60 mol. %.

9. The process of claim 1, wherein the vapor stream comprises said unreacted hydrogen in an amount between 90 to 100 mol. %.

10. The process of claim 1, wherein the concentration of at least one of the at least one by-product gas is substantially constant at steady state.

11. A process for producing ethanol comprising the steps of:
    hydrogenating acetic acid from an acetic acid feed stream in a reactor in the presence of a catalyst to form a crude ethanol product comprising ethanol;
    separating at least a portion of the crude ethanol product to yield a vapor stream and a liquid stream, wherein the vapor stream comprises unreacted hydrogen and carbon monoxide in an amount from 0.01 to 2 mol. %, and wherein the liquid stream comprises ethanol and at least one dissolved by-product gas;

purging at least a portion of at least one dissolved by-product gas from the liquid stream to form a second purge stream;
returning at least a portion of the vapor stream directly or indirectly to the reactor; and
recovering ethanol from the liquid stream.

12. The process of claim 11, wherein the vapor stream further comprises methane in an amount from 0.01 to 3 mol. %.

13. The process of claim 11, wherein the vapor stream further comprises ethane in an amount from 0.01 to 3 mol. %.

14. The process of claim 11, wherein the vapor stream further comprises carbon dioxide in an amount from 0.01 to 3 mol. %.

15. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

16. A process for producing ethanol comprising the steps of:
hydrogenating acetic acid from an acetic acid feed stream and a hydrogen feed stream in a reactor system in the presence of a catalyst to form a crude ethanol product comprising ethanol;
separating at least a portion of the crude ethanol product to yield a vapor stream and a liquid stream, wherein the vapor stream comprises unreacted hydrogen, and wherein the liquid stream comprises ethanol;
returning at least a portion of the vapor stream directly or indirectly to the reactor;
measuring a pressure of the vapor stream or a pressure of the at least a portion of the vapor stream;
controlling pressure in the reactor system by regulating the feed of fresh hydrogen to the reactor in response to the measured pressure; and
recovering ethanol from the liquid stream.

17. The process of claim 16, maintaining a substantially constant pressure in the reactor system.

18. The process of claim 16, wherein at least 85% of the gases separated from the crude ethanol product are returned to the reactor via vapor stream.

19. The process of claim 16, wherein the feed of fresh hydrogen is controlled to maintain a molar ratio of total hydrogen to acetic acid of at least 2:1 in the reactor.

20. A process for producing ethanol comprising the steps of:
hydrogenating acetic acid from an acetic acid feed stream in a reactor in the presence of a catalyst to form a crude ethanol product comprising ethanol;
separating the crude ethanol product to yield a vapor stream and a liquid stream, wherein the vapor stream comprises unreacted hydrogen and at least one by-product gas, and wherein the liquid stream comprises ethanol;
withdrawing a slip stream from the vapor stream;
purging a portion of the slip stream when the concentration of one of the at least one by-product gases is greater than 5 mol. %; and
recovering ethanol from the liquid stream.

21. The process of claim 20, further comprising monitoring the concentration of the at least one by-product gas.

22. The process of claim 20, further comprising maintaining a constant pressure in the reactor by regulating feed of fresh hydrogen to the reactor in response to the purged stream.

23. The process of claim 20, wherein the at least one by-product gas is selected from the group consisting of methane, ethane, carbon monoxide, carbon dioxide, nitrogen and mixtures thereof.

24. The process of claim 20, wherein the at least one by-product gas is carbon monoxide and wherein the slip stream is purged when the concentration of carbon monoxide is greater than 0.5 mol. %.

25. A process for producing ethanol comprising the steps of:
hydrogenating acetic acid from an acetic acid feed stream in a reactor in the presence of a catalyst to form a crude ethanol product comprising ethanol;
separating at least a portion of the crude ethanol product to yield a vapor stream and a liquid stream, wherein the vapor stream comprises unreacted hydrogen and at least one by-product gas, and wherein the liquid stream comprises ethanol and at least one dissolved by-product gas;
purging the at least one dissolved by-product gas from the liquid stream; and
recovering ethanol from the liquid stream.

26. The process of claim 25, further comprising returning the vapor stream directly or indirectly to the reactor.

27. The process of claim 25, wherein the vapor stream is not purged.

* * * * *